United States Patent
Lee et al.

(10) Patent No.: US 11,952,565 B2
(45) Date of Patent: Apr. 9, 2024

(54) ELECTRICAL STIMULATION DEVICE

(71) Applicant: SAMSUNG ELECTRONICS CO., LTD., Suwon-si (KR)

(72) Inventors: Don-Wook Lee, Seoul (KR); Young Jun Hong, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 511 days.

(21) Appl. No.: 17/147,662

(22) Filed: Jan. 13, 2021

(65) Prior Publication Data

US 2022/0064583 A1 Mar. 3, 2022

(30) Foreign Application Priority Data

Sep. 2, 2020 (KR) ........................ 10-2020-0111708

(51) Int. Cl.
 *C12M 1/42* (2006.01)
(52) U.S. Cl.
 CPC .................................. *C12M 35/02* (2013.01)
(58) Field of Classification Search
 None
 See application file for complete search history.

(56) References Cited

U.S. PATENT DOCUMENTS

| 9,211,400 | B2 | 12/2015 | Bachinski et al. | |
|---|---|---|---|---|
| 2009/0170178 | A1* | 7/2009 | Ozaki | C12M 23/10 |
| | | | | 435/289.1 |
| 2012/0244593 | A1* | 9/2012 | Huang | C12N 15/87 |
| | | | | 435/173.6 |

FOREIGN PATENT DOCUMENTS

| CN | 103525700 A | * 1/2014 | ............ C12M 23/12 |
|---|---|---|---|
| JP | 6042430 B2 | 12/2016 | |
| WO | WO 2013/012465 A1 | 1/2013 | |

OTHER PUBLICATIONS

Ivorra et al. "Impedance Analyzer for in vivo Electroporation Studies", Proceedings of the 28th IEEE EMBS Annual International Conference New York City, USA, Aug. 30-Sep. 3, 2006, pp. 5056-5059. (Year: 2006).*
Rorsman, Patrik, and Frances M. Ashcroft. "Pancreatic β-Cell Electrical Activity and Insulin Secretion: Of Mice and Men." *Physiological reviews* 98.1 (2018): 117-214. (98 pages in English).
Krawczyk, Krzysztof, et al. "Electrogenetic cellular insulin release for real-time glycemic control in type 1 diabetic mice." *Science* 368.6494 (2020): 993-1001. (10 pages in English).

* cited by examiner

*Primary Examiner* — William H. Beisner
(74) *Attorney, Agent, or Firm* — NSIP Law

(57) ABSTRACT

An electrical stimulation device includes a terminal electrode having an opening at a center thereof, a ground electrode having an area smaller than that of the terminal electrode, and a power source connected to the terminal electrode and the ground electrode and configured to apply an electrical stimulus to an object disposed between the terminal electrode and the ground electrode by applying a terminal voltage to the terminal electrode.

18 Claims, 5 Drawing Sheets

ELECTRICAL STIMULATION DEVICE

CROSS-REFERENCE TO RELATED APPLICATIONS

This application claims the benefit under 35 USC § 119(a) of Korean Patent Application No. 10-2020-0111708 filed on Sep. 2, 2020, in the Korean Intellectual Property Office, the entire disclosure of which is incorporated herein by reference for all purposes.

BACKGROUND

1. Field

The following description relates to a device for electrical stimulation, and more particularly, to a technology for regulating a potential difference of a cell membrane through electrical stimulation.

2. Description of Related Art

A cell is surrounded by a cell membrane and includes a cell nucleus and cytoplasm. The cell membrane, which is a boundary that distinguishes inside and outside the cell, transfers an external substance inside and an internal substance outside. The cell membrane regulates a potential difference between the inside and the outside of the cell to allow a substance to move. By disposing an electrode structure around the cell membrane and applying an electric field to the electrode structure, it is possible to regulate the potential difference of the cell membrane, thereby inducing the internal and external substances of the cell to move.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a device for electrical stimulation includes a terminal electrode having an opening at a center thereof, a ground electrode having an area smaller than that of the terminal electrode, and a power source connected to the terminal electrode and the ground electrode. The power source is configured to apply an electrical stimulus to an object disposed between the terminal electrode and the ground electrode by applying a terminal voltage to the terminal electrode.

The terminal electrode may be in a shape of a circle or a polygon.

The opening of the terminal electrode may be in a shape of a circle or a polygon.

The ground electrode may be in a shape of a circle or a polygon.

A distance between the terminal electrode and the object may be greater than a distance between the ground electrode and the object.

In another general aspect, a device for electrical stimulation includes a first terminal electrode having a first opening at a center thereof, a first ground electrode disposed on an opposite side to the first terminal electrode with respect to an object disposed therebetween and having an area smaller than that of the first terminal electrode, a second terminal electrode having a second opening at a center thereof, a second ground electrode disposed on an opposite side to the second terminal electrode with respect to the object disposed therebetween and having an area smaller than that of the second terminal electrode, and a power source. The second ground electrode is disposed at a center of the first opening, and the first ground electrode is disposed at a center of the second opening. The power source is configured to apply an electrical stimulus to the object by applying a terminal voltage alternately to a pair of the first terminal electrode and the first ground electrode and a pair of the second terminal electrode and the second ground electrode.

The first terminal electrode or the second terminal electrode may be in a shape of a circle or a polygon.

The first opening or the second opening may be in a shape of a circle or a polygon.

The first ground electrode or the second ground electrode may be in a shape of a circle or a polygon.

A distance between the first terminal electrode or the second terminal electrode and the object may be greater than a distance between the first ground electrode or the second ground electrode and the object.

In still another general aspect, a device for electrical stimulation includes a terminal layer, an object layer including one or more objects, a ground layer, and a power source. The terminal layer and the ground layer include a plurality of electrode structures. Each of the electrode structure includes a first terminal electrode having a first opening at a center thereof, a first ground electrode disposed at a center of a second opening, disposed on an opposite side to the first terminal electrode with respect to the object layer, and having an area smaller than that of the first terminal electrode, a second terminal electrode having the second opening at a center thereof, and a second ground electrode disposed at a center of the first opening, disposed on an opposite side to the second terminal electrode with respect to the object layer, and having an area smaller than that of the second terminal electrode. The power source is configured to apply an electrical stimulus to the objects included in the object layer by applying a terminal voltage alternately to a pair of the first terminal electrode and the first ground electrode of each of the electrode structures and a pair of the second terminal electrode and the second ground electrode of each of the electrode structures.

The first terminal electrode or the second terminal electrode may be in a shape of a circle or a polygon.

The first opening or the second opening may be in a shape of a circle or a polygon.

The first ground electrode or the second ground electrode may be in a shape of a circle or a polygon.

The objects may be arranged in one layer of the object layer.

The objects may be arranged in a lattice pattern in the object layer.

Other features and aspects will be apparent from the following detailed description, the drawings, and the claims.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
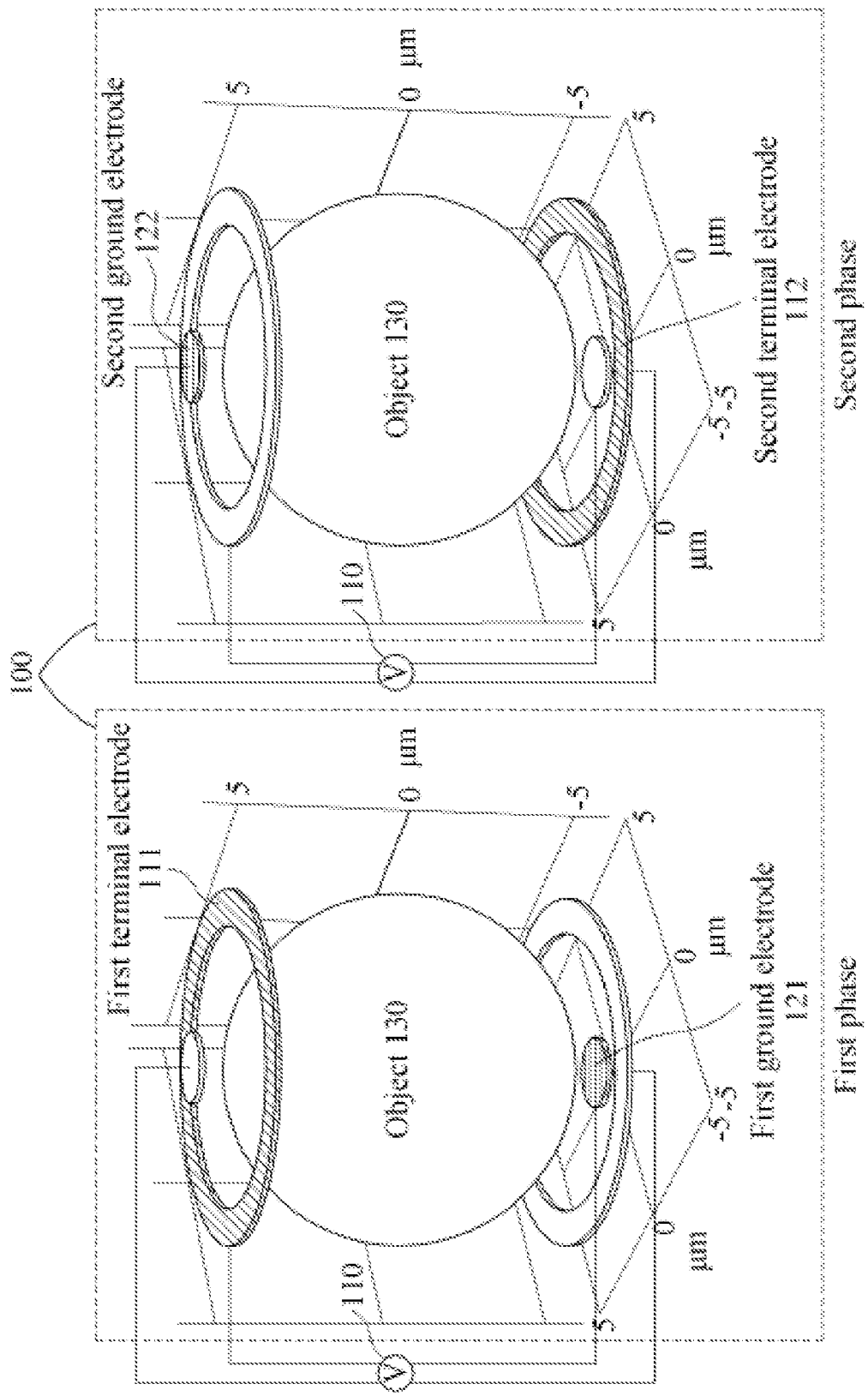
FIG. 1 illustrates an example of an operation of a device for electrical stimulation.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The terminology used herein is for the purpose of describing particular examples only, and is not to be used to limit the disclosure. As used herein, the singular forms "a," "an," and "the" are intended to include the plural forms as well, unless the context clearly indicates otherwise. As used herein, the term "and/or" includes any one and any combination of any two or more of the associated listed items. As used herein, the terms "include," "comprise," and "have" specify the presence of stated features, numbers, operations, elements, components, and/or combinations thereof, but do not preclude the presence or addition of one or more other features, numbers, operations, elements, components, and/or combinations thereof.

In addition, terms such as first, second, A, B, (a), (b), and the like may be used herein to describe components. Each of these terminologies is not used to define an essence, order, or sequence of a corresponding component but used merely to distinguish the corresponding component from other component(s).

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween. Likewise, expressions, for example, "between" and "immediately between" and "adjacent to" and "immediately adjacent to" may also be construed as described in the foregoing.

Unless otherwise defined, all terms, including technical and scientific terms, used herein have the same meaning as commonly understood by one of ordinary skill in the art to which this disclosure pertains consistent with and after an understanding of the present disclosure. Terms, such as those defined in commonly used dictionaries, are to be interpreted as having a meaning that is consistent with their meaning in the context of the relevant art and the present disclosure, and are not to be interpreted in an idealized or overly formal sense unless expressly so defined herein.

Also, in the description of the examples, detailed description of structures or functions that are thereby known after an understanding of the disclosure of the present application will be omitted when it is deemed that such description will cause ambiguous interpretation of the example embodiments.

Hereinafter, examples will be described in detail with reference to the accompanying drawings, and like reference numerals in the drawings refer to like elements throughout.

FIG. 1 illustrates an example of an operation of a device for electrical stimulation. The device for electrical stimulation will be simply referred to hereinafter as an electrical stimulation device.

A cell membrane is a fluid mosaic structure having a dual layer of phospholipid that is referred to as a phospholipid bilayer. Here, a fluid mosaic indicates a two-dimensional (2D) flow in which phospholipid floats freely. By the phospholipid bilayer, inside and outside of a cell may be electrically isolated.

Inside the cell membrane, there is a protein that functions as a path or receptor crossing the cell membrane. Here, a membrane protein disposed across the bilayer of the cell membrane is also referred to as a transmembrane protein. The membrane protein includes a transporter protein, or simply a transporter, for example, a sodium-potassium pump, that transports a material or substance.

The inside and the outside of the cell is electrically isolated based on the cell membrane, and have a potential difference due to a difference in ion concentration. In a resting potential state, an amount of sodium ions flowing out is greater than an amount of potassium ions flowing in, and there is a greater amount of negative charges inside. Thus, in the resting potential state, the inside has a potential less than that of the outside and is thus in a polarization state. Here, with respect to an inner potential (Vin) and an outer potential (Vout), a membrane potential difference (Vm) is defined as Vin−Vout, or Vm=Vin−Vout. It is between −20 millivolts (mV) and −100 mV in a case of a mammalian cell. In general, it is −70 mV in a case of a neuron, −90 mV in a case of a muscle cell, and −50 mV in a case of an epithelial cell.

In a case of stimulating a certain cell, an outflow of potassium ions may decrease, thereby causing depolarization in which a membrane potential difference decreases. A potential in such a depolarization state is referred to as an action potential. Under an actual condition of a cell membrane, depolarization of 30 mV may be induced by an electric field of 3 volts per millimeter (V/mm) within 2 microseconds (μs).

In an example, an electrical stimulation device 100 may artificially induce a potential difference by applying an electrical stimulus to an object. The electrical stimulation device 100 may induce a desired potential different by applying an electrical stimulus to an object through an asymmetric electrode structure. The electrical stimulation device 100 may induce depolarization by applying an electrical stimulation to an object. Here, the object may include a cell.

In the example, the electrical stimulation device 100 includes a terminal electrode, a ground electrode, and a power source 110. The terminal electrode and the ground electrode may be connected to the power source 110. The power source 110 may apply an electrical stimulus to an object disposed between the terminal electrode and the ground electrode by applying a terminal voltage to the terminal electrode. A current stimulus to be applied may be between 0.01 microampere (μA) and 10 μA for a single cell, and a terminal potential may be less than 1 volt (V) for a single cell.

The power source 110 may apply a positive voltage to the terminal electrode and a negative voltage to the ground electrode. Thus, a negative potential may be induced to an outer surface of a cell membrane near the ground electrode, and a positive potential may be induced to an inner surface of the cell membrane. Thus, around the cell membrane near the ground electrode, a depolarization state may be induced.

For example, in a case in which an object includes a beta cell forming a pancreatic tissue, the beta cell may recognize an increase in a glucose concentration and become depolarized, and then secrete insulin. In this example, the electrical stimulation device 100 may apply an electrical stimulus to the beta cell to induce such a depolarization state and the secretion of insulin.

While the depolarization state is induced in the cell membrane around the ground electrode, a hyperpolarization state may be induced in the cell membrane around the terminal electrode. Here, when the depolarization and the hyperpolarization are induced to the same level, an effect of the depolarization in cell stimulation may be reduced by half. Here, by inducing a relatively higher depolarizing potential difference and inducing a relatively lower hyperpolarizing potential difference, it is possible to expand a range of the cell membrane to be stimulated by the depolarization.

An area of the terminal electrode of the electrical stimulation device 100 may be greater than an area of the ground electrode of the electrical stimulation device 100. When an area of an electrode decreases, a higher potential may be applied for maintaining a same terminal current. When the area of the ground electrode decreases, a higher potential may be applied to the ground electrode, and a depolarizing potential difference of the cell membrane around the ground electrode may have a greater value. When the area of the terminal electrode increases, a lower potential may be applied to the terminal electrode, and a hyperpolarizing potential difference of the cell membrane around the terminal electrode may have a smaller value. Thus, a depolarization effect may be more intensified compared to a hyperpolarization effect.

A distance between the ground electrode and an object may be less than a distance between the terminal electrode and the object. In a case in which a same voltage is applied, a higher potential difference may be induced when a distance between an electrode and a cell membrane decreases. When the distance between the ground electrode and the object is less than the distance between the terminal electrode and the object, the depolarization may be intensified further and the hyperpolarization may be weakened further. For example, an interval between the terminal electrode and the object may be greater than 4 μm, and an internal between the ground electrode and the object may be greater than 0 μm. The ground electrode may be in contact with the object.

In another example, the electrical stimulation device 100 may include two pairs of electrode structures. For example, referring to FIG. 1, the electrical stimulation device 100 includes an electrode pair of a first terminal electrode 111 and a first ground electrode 121 and an electrode pair of a second terminal electrode 112 and a second ground electrode 122. The first ground electrode 121 may be disposed on an opposite side to the first terminal electrode 111 with respect to an object 130 disposed therebetween. The second ground electrode 122 may be disposed on an opposite side to the second terminal electrode 112 with respect to the object 130 disposed therebetween.

An area of the first terminal electrode 111 may be greater than an area of the first ground electrode 121. An area of the second terminal electrode 112 may be greater than an area of the second ground electrode 122. An internal diameter of each terminal electrode may be greater than an external diameter of each ground electrode. A diameter of the object 130 may be greater than the external diameter of each ground electrode.

Each terminal electrode may have an opening at a center thereof. For example, each terminal electrode may be in a shape of a doughnut, a circular band, or a ring. An outer circumference of each terminal electrode may be in various shapes. For example, each terminal electrode may be in a shape of a circle or a polygon. An inner circumference of each terminal electrode may be in various shapes. For example, the opening of each terminal electrode may be in a shape of a circle or a polygon.

The second ground electrode 122 may be disposed in the opening of the first terminal electrode 111. The first ground electrode 121 may be disposed in the opening of the second terminal electrode 112. Through the opening of the first terminal electrode 111, an electric field applied to the electrode pair of the second terminal electrode 112 and the second ground electrode 122 may not be hindered by the first terminal electrode 111 in a second phase. Similarly, through the opening of the second terminal electrode 112, an electric field applied to the electrode pair of the first terminal electrode 111 and the first ground electrode 121 may not be hindered by the second terminal electrode 112 in a first phase.

The electrical stimulation device 100 may further intensify the induction of the depolarization by alternately applying a biphasic electrical stimulus. In the first phase, the electrical stimulation device 100 may apply a voltage to the electrode pair of the first terminal electrode 111 and the first ground electrode 121 for a first time period. By this, depolarization may be induced in an area of the object 130 around the first ground electrode 121. In the second phase, the electrical stimulation device 100 may apply a voltage to the electrode pair of the second terminal electrode 112 and the second ground electrode 122 for a second time period. By this, depolarization may be induced in an area of the object 130 around the second ground electrode 122. Here, the first time period and the second time period may form one cycle. By adjusting the first time period and the second time period, it is possible to maximize the depolarization.

Figure 2:
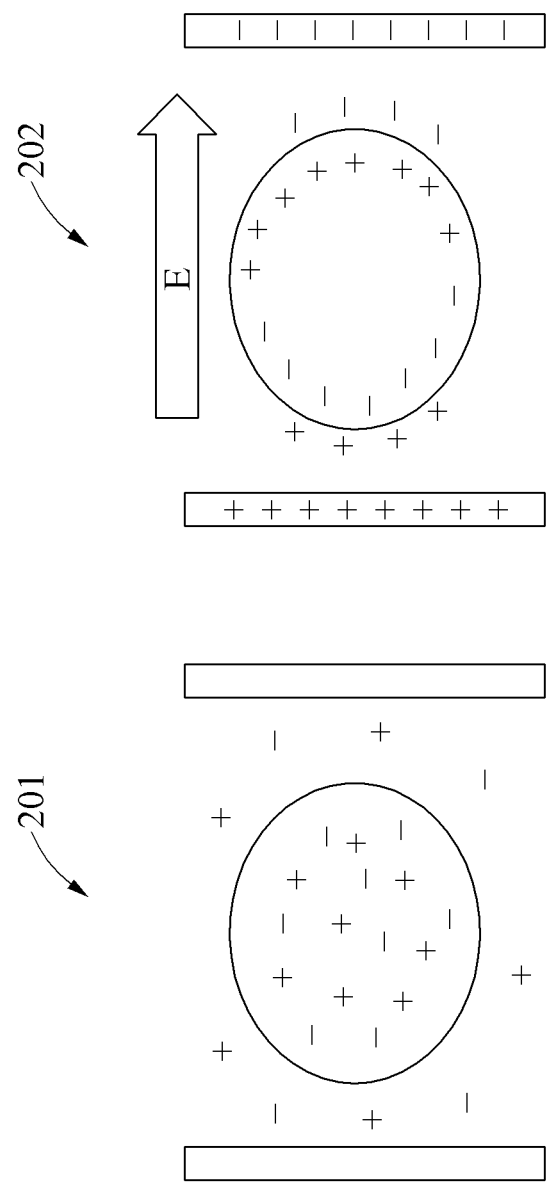
FIG. 2 illustrates an example of a distribution of electric charges inside and outside a cell disposed between electrodes based on the presence or absence of an electric field.

FIG. 2 illustrates an example of a distribution of electric charges inside and outside a cell disposed between electrodes based on the presence or absence of an electric field.

Referring to FIG. 2, a left portion 201 indicates a distribution of electric charges inside and outside a cell when a voltage is not applied to an electrode. In such a case, the electric charges may be naturally distributed inside and outside the cell. In a resting potential state, there may be a polarization state in which an inner potential is less than an outer potential.

A right portion 202 indicates a distribution of electric charges inside and outside a cell when a voltage is applied to an electrode. When a positive voltage is applied to an electrode on a left side and a negative voltage is applied to an electrode on a right side as illustrated, both hemispheres of the cell may inevitably become a hyperpolarization state and a depolarization state, respectively.

Figure 3:
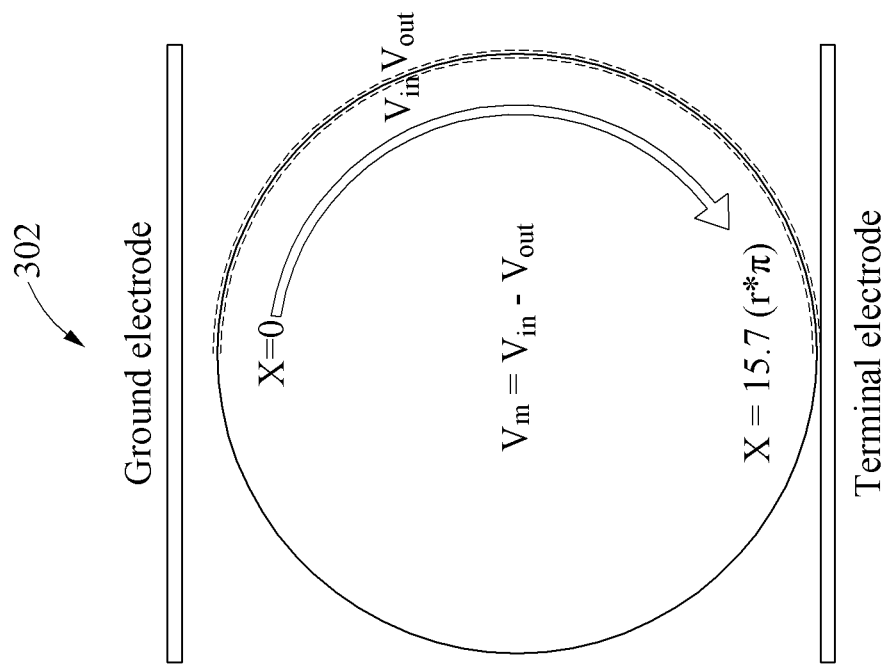
FIG. 3 illustrates an example of a comparison between an asymmetric electrode structure of a device for electrical stimulation and an existing symmetric electrode structure.
Figure 3:
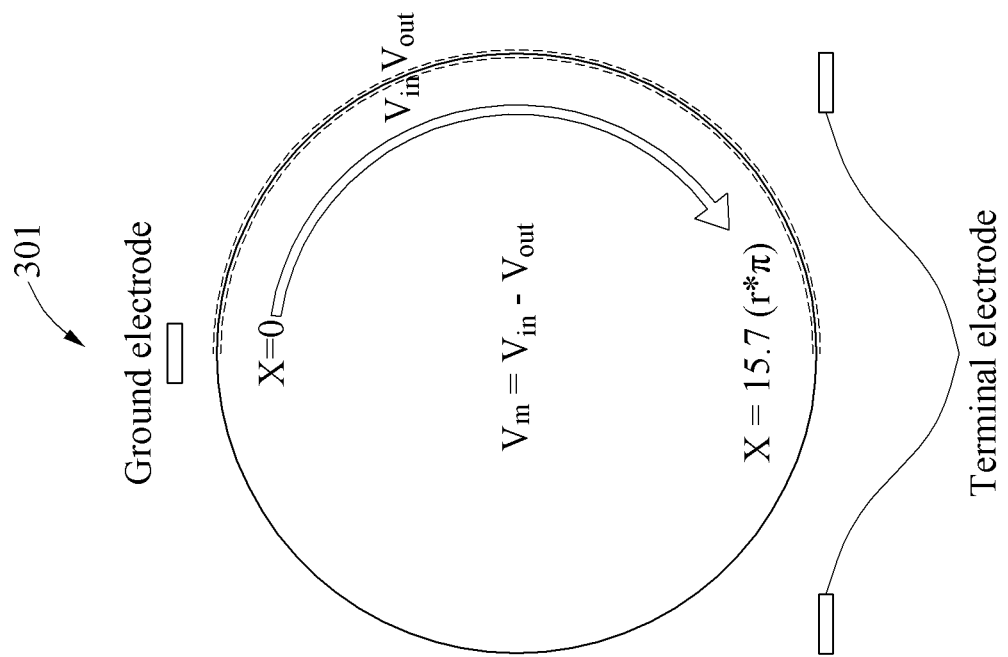

FIG. 3 illustrates an example of a comparison between an asymmetric electrode structure of an electrical stimulation device and an existing symmetric electrode structure.

A potential difference of a cell membrane is defined as $Vm=Vin-Vout$, and a length X of a hemisphere of a cell is 15.7 ($r*\pi$). Here, Vin denotes an inner potential or a potential inside the cell, and Vout denotes an outer potential or a potential outside the cell.

Referring to FIG. 3, in a case of an asymmetric electrode 301, an area of a ground electrode is relatively small and an area of a terminal electrode is relatively large, and thus a higher potential may occur at the ground electrode and a lower potential may occur at the terminal electrode. Thus, depolarization may be induced in a greater area from the ground electrode.

In a case of a symmetric electrode 302, an area of a ground electrode and an area of a terminal electrode are equal. In such a case, a potential of the ground electrode and a potential of the terminal electrode may be equal. Thus, a range of depolarization around the ground electrode may become smaller than that in the case of the asymmetric electrode 301.

Figure 4:
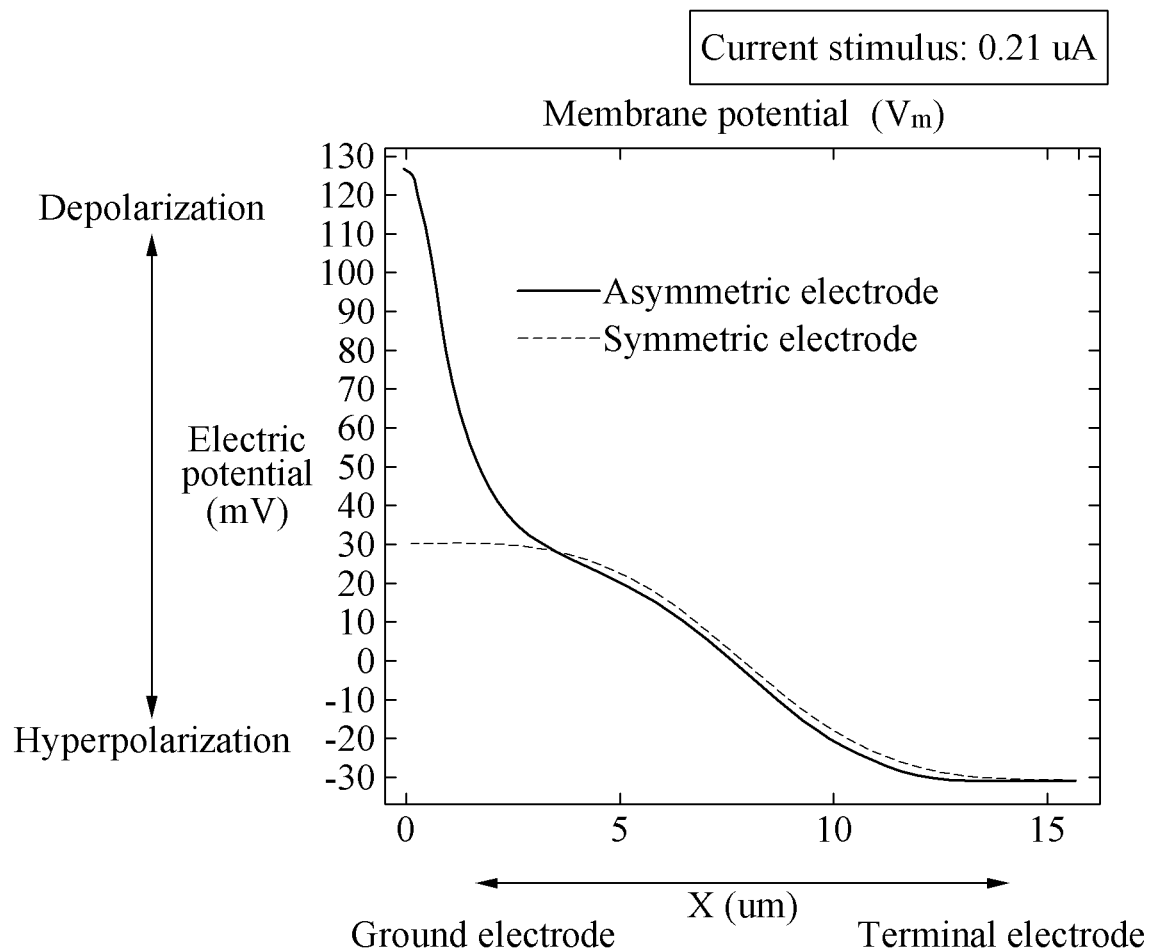
FIG. 4 illustrates an example of a graph of a membrane potential in an asymmetric electrode structure and in a symmetric electrode structure.

FIG. 4 illustrates an example of a graph of a membrane potential in an asymmetric electrode structure and in a symmetric electrode structure.

FIG. 4 illustrates a change in potential from a ground electrode to a terminal electrode in a case in which a current stimulus of 0.21 µA is applied to each terminal in an asymmetric electrode and a symmetric electrode. In a case of the symmetric electrode, depolarization of 30 mV may occur in an area near the ground electrode and hyperpolarization of −30 mV may occur in an area near the terminal electrode. In contrast, in a case of the asymmetric electrode, depolarization exceeding 120 mV may occur in the area near the ground electrode and hyperpolarization of −30 mV may occur in the area near the terminal electrode.

As described above, in a case in which an area of the ground electrode is small, a higher potential may be applied to the ground electrode, and a depolarizing potential difference of a cell membrane near the ground electrode may have a greater value. However, in a case in which an area of the terminal electrode is large, a lower potential may be applied to the terminal electrode, and a hyperpolarizing potential difference of the cell membrane near the terminal electrode may have a smaller value. Thus, a depolarization effect may be intensified more compared to a hyperpolarization effect.

Figure 5:
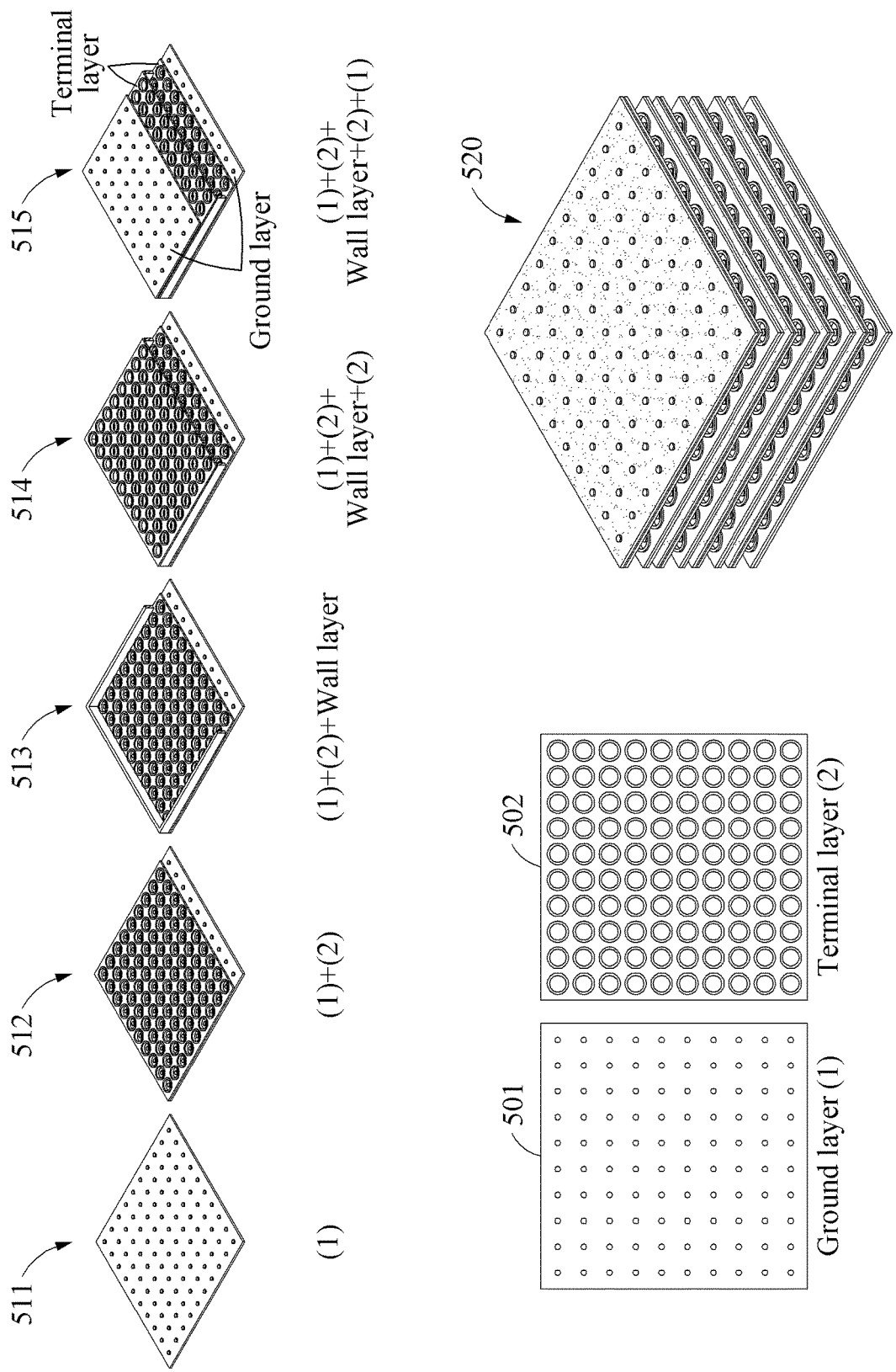
FIG. 5 illustrates an example of a structure of a device for electrical stimulation.

FIG. 5 illustrates another example of a structure of an electrical stimulation device.

According to another example, an electrical stimulation device includes a terminal layer 502, an object layer including one or more objects, a ground layer 501, and a power source. The terminal layer 502 and the ground layer 501 may include a plurality of electrode structures.

Each of the electrode structures may include a first terminal electrode having a first opening at a center thereof, a first ground electrode, a second terminal electrode having a second opening at a center thereof, and a second ground electrode. Here, the first ground electrode may be disposed at a center of the second opening, disposed on an opposite side to the first terminal electrode with the object layer at a center, and having an area smaller than that of the first terminal electrode. The second ground electrode may be disposed at a center of the first opening, disposed on an opposite side to the second terminal electrode with the object layer at a center, and having an area smaller than that of the second terminal electrode.

The power source may apply an electrical stimulus to the objects included in the object layer disposed between the first terminal electrode and the first ground electrode by applying a terminal voltage alternately to a pair of the first terminal electrode and the first ground electrode in each of the electrode structures and a pair of the second terminal electrode and the second ground electrode in each of the electrode structures.

The first terminal electrode or the second terminal electrode may be in a shape of a circle or a polygon. The first opening or the second opening may be in a shape of a circle or a polygon. The first ground electrode or the second ground electrode may be in a shape of a circle or a polygon.

The electrical stimulation device may apply an electrical stimulus to a single cell or a plurality of cells. The objects may be arranged in one layer of the object layer. The cells may be arranged in one layer of a 2D plane. The cells may be arranged in a regular or irregular pattern in one layer of the 2D plane. The objects may be arranged in a lattice pattern in the object layer.

Referring to FIG. 5, conductors each having a relatively small area may be arranged on the ground layer 501 in a lattice pattern, and doughnut-shaped conductors each having a relatively large area may be arranged on the terminal layer 502 in a lattice pattern. Each of the conductors in the ground layer 501 may be matched to an inside of each of the conductors in the terminal layer 502.

A series of steps 511 through 515 may be performed to manufacture the electrical stimulation device of one layer as illustrated. In step 511, the ground layer 501 is disposed. In step 512, the terminal layer 502 is disposed on the ground layer 501. In step 513, a wall layer for forming the object layer is disposed at an edge of a structure obtained in step 512. In step 514, the terminal layer 502 is disposed on the wall layer. In step 515, the ground layer 501 is disposed on the terminal layer 502. Then, manufacturing the electrical stimulation device of one layer may be completed. The electrical stimulation device may also be provided in a plurality of layers. For example, the electrical stimulation device may be provided in four layers 520.

The units described herein may be implemented using hardware components and software components. For example, the hardware components may include microphones, amplifiers, band-pass filters, audio to digital convertors, non-transitory computer memory and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums. The non-transitory computer readable recording medium may include any data storage device that can store data which can be thereafter read by a computer system or processing device. Examples of the non-transitory computer readable recording medium include read-only memory (ROM), random-access memory (RAM), CD-ROMs, magnetic tapes, floppy disks, optical data storage devices. Also, functional programs, codes, and code segments that accomplish the examples disclosed herein can be easily construed by programmers skilled in the art to which the examples pertain based on and using the flow diagrams and block diagrams of the figures and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

What is claimed is:

1. A device for electrical stimulation, comprising:
   a first terminal electrode having a first opening at a center thereof;
   a second terminal electrode having a second opening at a center thereof;
   a first ground electrode having an area smaller than an area of the first terminal electrode;
   a second ground electrode having an area smaller than an area of the second terminal electrode; and
   a power source configured to apply an electrical stimulus to an object disposed between a pair of the first terminal electrode and the first ground electrode and a pair of the second terminal electrode and the second ground electrode by applying a terminal voltage alternately to the pair of the first terminal electrode and the first ground electrode and the pair of the second terminal electrode and the second ground electrode.

2. The device of claim 1, wherein the first and second terminal electrodes are in a shape of a circle or a polygon.

3. The device of claim 1, wherein the first and second openings are in a shape of a circle or a polygon.

4. The device of claim 1, wherein the first and second ground electrodes are in a shape of a circle or a polygon.

5. The device of claim 1, wherein a distance between the first terminal electrode and the object is greater than a distance between the first ground electrode and the object.

6. The device of claim 1, wherein a diameter of the first opening of the first terminal electrode is greater than a diameter of the first ground electrode, and the diameter of the first ground electrode is lesser than a diameter of the object.

7. The device of claim 1, wherein a portion of the object is disposed in the first opening of the first terminal electrode, and the first ground electrode is in contact with the object.

8. A device for electrical stimulation, comprising:
   a first terminal electrode having a first opening at a center thereof;
   a first ground electrode disposed on an opposite side to the first terminal electrode with respect to an object disposed therebetween and having an area smaller than an area of the first terminal electrode;
   a second terminal electrode having a second opening at a center thereof;
   a second ground electrode disposed on an opposite side to the second terminal electrode with respect to the object disposed therebetween and having an area smaller than an area of the second terminal electrode; and
   a power source,
   wherein the second ground electrode is disposed at a center of the first opening,
   the first ground electrode is disposed at a center of the second opening, and
   the power source is configured to apply an electrical stimulus to the object by applying a terminal voltage alternately to a pair of the first terminal electrode and the first ground electrode and a pair of the second terminal electrode and the second ground electrode.

9. The device of claim 8, wherein one or both of the first terminal electrode and the second terminal electrode is in a shape of a circle or a polygon.

10. The device of claim 8, wherein one or both of the first opening and the second opening is in a shape of a circle or a polygon.

11. The device of claim 8, wherein one or both of the first ground electrode and the second ground electrode is in a shape of a circle or a polygon.

12. The device of claim 8, wherein a distance between one or both of the first terminal electrode and the second terminal electrode and the object is greater than a distance between one or both of the first ground electrode and the second ground electrode and the object.

13. A device for electrical stimulation, comprising:
   a first terminal layer comprising one or more terminal electrodes;
   a second terminal layer comprising one or more terminal electrodes;
   an object layer comprising one or more objects;
   a first ground layer comprising one or more ground electrodes;
   a second ground layer comprising one or more ground electrodes;
   a power source;

a first terminal electrode, of the first terminal layer, having a first opening at a center thereof;
a first ground electrode, of the first ground layer, disposed at a center of a second opening, the first ground electrode being disposed on an opposite side to the first terminal electrode with respect to the object layer, and having an area smaller than an area of the first terminal electrode;
a second terminal electrode, of the second terminal layer, having the second opening at a center thereof; and
a second ground electrode, of the second ground layer, disposed at a center of the first opening, the second ground electrode being disposed on an opposite side to the second terminal electrode with respect to the object layer, and having an area smaller than an area of the second terminal electrode,
wherein the power source is configured to apply an electrical stimulus to the one or more objects by applying a terminal voltage alternately to a pair of the first terminal electrode and the first ground electrode and a pair of the second terminal electrode and the second ground electrode.

14. The device of claim 13, wherein one or both of the first terminal electrode and the second terminal electrode is in a shape of a circle or a polygon.

15. The device of claim 13, wherein one or both of the first opening and the second opening is in a shape of a circle or a polygon.

16. The device of claim 13, wherein one or both of the first ground electrode and the second ground electrode is in a shape of a circle or a polygon.

17. The device of claim 13, wherein the one or more objects are arranged in one layer of the object layer.

18. The device of claim 13, wherein the one or more objects are arranged in a lattice pattern in the object layer.

* * * * *